Figure 1:
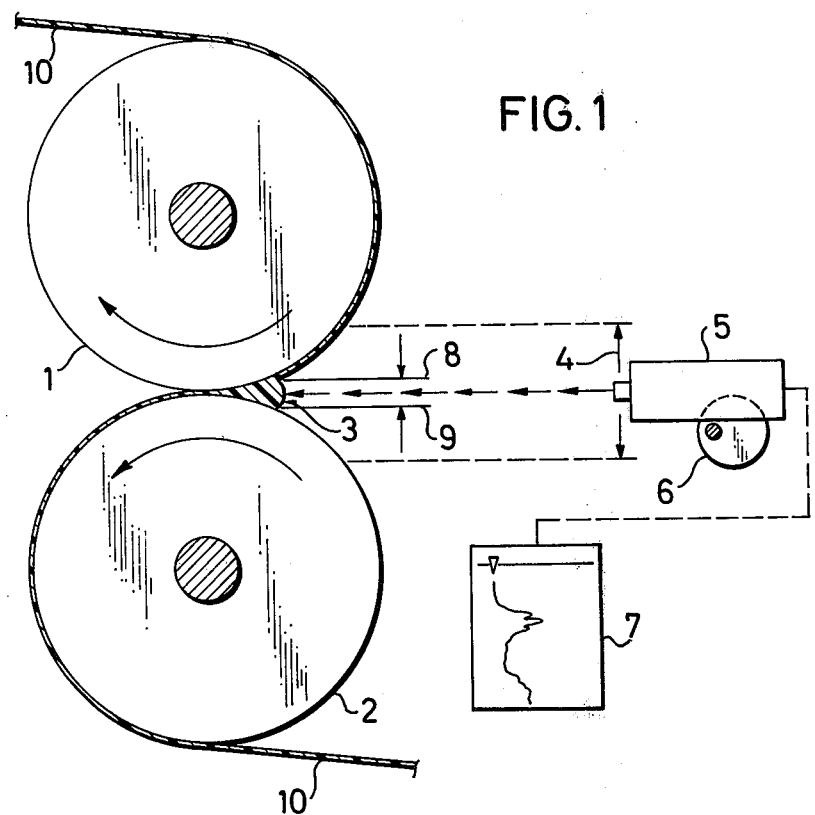

United States Patent [19]

Maier et al.

[11] 3,962,580

[45] June 8, 1976

[54] INFRARED PROCESS FOR MEASURING THE KNEADING MASS IN A CALENDER ROLLER GAP

[75] Inventors: Franz Maier, Burgkirchen, Alz; Walter Niederstatter, Mehring-Od; Hans-Rainer Stümpf, Burgkirchen, Alz, all of Germany

[73] Assignee: Hoechst Aktiengesellschaft, Frankfurt am Main, Germany

[22] Filed: Dec. 13, 1974

[21] Appl. No.: 532,416

[30] Foreign Application Priority Data

Dec. 20, 1973 Germany............................ 2363467

[52] U.S. Cl............................ 250/340; 250/358 R
[51] Int. Cl.².......................................... G01N 23/00
[58] Field of Search........................... 250/339–342, 250/347–353, 560, 358, 360

[56] References Cited
UNITED STATES PATENTS 3,532,887  10/1970  Clark ................................. 250/347
3,805,072  4/1974  Goerens et al...................... 250/342

*Primary Examiner*—Davis L. Willis
*Attorney, Agent, or Firm*—Connolly and Hutz

[57] ABSTRACT

The thickness of a thermoplastic kneading mass having a temperature of at least 40°C in the feeding region of a roller gap, is measured by scanning in the said feeding region the zone of bare roll to kneading mass and kneading mass to rolling sheet with an infrared radiation receiver of high geometrical resolution defined by a diameter of the measuring field of from 0.5 to 3 mm with a measuring distance of from 0.2 to 3 m, recording the curve of thermal radiation and determining the thickness of kneading mass from the distance of the two points of discontinuity in the recorded curve of thermal radiation with consideration of the ratio of the scanning speed to the speed of registration.

1 Claim, 2 Drawing Figures

U.S. Patent June 8, 1976 3,962,580

INFRARED PROCESS FOR MEASURING THE KNEADING MASS IN A CALENDER ROLLER GAP

This invention relates to a process for measuring without contact the bank of a thermoplastic kneading mass of at least 40°C in the feeding range of a roller during calendering.

The thickness of the accumulated material, the so-called bank of kneading mass, is one of the most important operating parameters in the shaping of plastic materials by rolling. On the one hand, a minimum amount of accumulated material in the roller gap must be present to insure that the rolls do not get into direct contact with each other and are not damaged, on the other hand, too large a bank of kneading material would impair the quality of the final product. With a large accumulation of material in the roller gap the material may be thermally decomposed. It has been observed that with an optimum cigar-like shape of the kneading mass mostly extending over the whole width of the roll, flow troubles causing variations in thickness in the form of streaks and flow lines in the finished product and reducing its quality occur to a limited extent only.

German Auslegeschrift No. 1,504,723 describes a device comprising a sensing element fastened on a support and connected with a transformer by which the kneading mass is mechanically scanned. The supporting means lie with rolls on one of the calender rolls. It prevents a free access to every point of the kneading mass which is necessary for a normal course of production. The contact pressure of the sensing element may adulterate the measuring results. The heat conduction through the sensing element may interfere with the temperature and flowing conditions in the kneading mass. Finally, the danger exists that the sensing element is pushed to the side by occasionally occuring irregularities in the kneading mass and pulled in between the calender rolls whereby it is crushed, which may cause considerable damage.

German Offenlegungsschrift No. 2,141,741 proposes to project the outline of the kneading mass with the aid of a source of coherence radiation, mounted laterally on the calender, on a photo receiver system at the opposite side. The drawback of this process resides in the fact that only the maximum expansion of the kneading mass is measured and that no message is given about the profile of the kneading mass, which is an important operation parameter.

It is the object of the present invention to measure the size of the bank of kneading mass at a distance from the feeding gap of the calender roll which does not disturb the production and does not interfere with the kneading mass and optionally to determine the profile of the kneading mass over the entire width of the rolls.

The present invention provides a process for measuring without contact the bank of kneading mass in the feeding region of the roller gap, which comprises registering the curve of thermal radiation of the zone of bare roll - kneading mass - rolling sheet by means of an infrared radiation receiver of high geometric resolution power, defined by a diameter of the measuring field of from 0.5 to 3 mm at a measuring distance of from 0.2 to 3 m, and determining the bank of kneading mass by the distance of the two points of discontinuity in the recorded curve with consideration of the ratio of the scanning speed to the speed of registration.

When the curve of the thermal radiation is recorded in the inlet region of the roller gap fed with thermoplastic material from the side of the bare roll, a curve is obtained which takes at first an approximately horizontal course on a low level according to the very weak emission of radiation of the bare roll. In the further course of the curve, a distinct jump occurs as soon as the kneading mass in the feeding region of the roller gap is scanned. As compared to the rolling sheet running on the one roll this kneading mass has a distinctly higher surface temperature owing to the shear work which is transformed into heat in the said mass. Finally, the curve takes an approximately horizontal course on a mean level corresponding to the higher radiation emission of the rolling sheet as compared with the bare roll. It is also possible, of course, to record in reverse direction, i.e. rolling sheet, kneading mass, bare roll. It has surprisingly been found that the recorded curve of radiation has one distinct point of discontinuity each on either side of the jump, corresponding to the transition points of bare roll to kneading mass and kneading mass to rolling sheet, respectinely. The registration of these points of discontinuity permits an exact determination of the bank size of the kneading material because the recorded distance between the two points of discontinuity is proportional to the amount of kneading mass with consideration of the ratio of scanning speed to the speed of registration. In the case of the ratio being equal to 1, the amount of kneading mass directly arises from the scanning path, otherwise the proportionality factor corresponding to the respective ratio has to be taken into consideration.

The process according to the invention can be used in rolling and calendering processes of known thermoplastic materials such as polyvinyl chloride, polystyrene, polyolefins, acrylonitrile-butadiene-styrene polymers and copolymers thereof, as well as in processes of this type using other viscous materials, for example rubber mixtures.

The process according to the invention can be carried out with commercial infrared radiation receivers from a minimum temperature of the thermoplastic material of 40°C upward. The infrared radiation receiver used shall have a high geometric resolution, i.e. a small diameter of the measuring field of from 0.5 to 3 mm with a measuring distance of 0.2 to 3 m, preferably of from 0.5 to 1.5 mm with a measuring distance to the kneading mass of from 0.5 to 1.5 m.

The gap is preferably formed by two rolls. It may also be formed, however, by one roll and another stationary element. Scanning is advantageously performed in vertical direction with respect to the roller gap, and in the case of rolls of equal diameter preferably parallel to the connecting plane of the axes of the two rolls. Measuring by oblique scanning is also possible (in an angle of little less than 90° down to 30° with respect to the roller axis), but in this case a corresponding angle correction must be taken into consideration.

The process according to the invention permits not only to measure the amount of kneading mass but also it gives automatically in known manner the temperature curve, since with each corresponding calibration of the radiation receiver with consideration of the emission factor the recorded transient value of the receiver signal corresponds to the surface temperature of the scanned point.

The advantage achieved by the process of the invention resides in the fact that, instead of an inaccurate mechanical scanning of the kneading mass, the amount of kneading mass is measured without touching it from a distance which insure that rolling is not hindered. More particularly, the profile of the kneading mass can be determined over the whole length of the roller gap. This can be done by recording the heat radiation at many points along the gap by a movable receiver or by firmly installing a plurality of radiation receivers along the roller gap.

Figure 2:
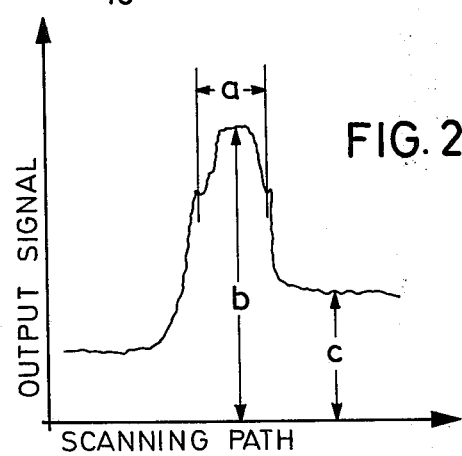

The invention will now be described in further detail and by way of example with reference to the accompanying drawing wherein:

FIG. 1 is a diagrammatic view of an arrangement suitable to carry out the process of the invention and FIG. 2 shows a recorded radiation curve.

An infrared radiation receiver 5, which can be displaced vertically over distance 4 by a rotating disk 6, is positioned in front of the feeding gap of the two rolls 1 and 2 containing the bank of kneading mass 3 to be measured, the distance 4 being chosen in such a manner that part of the bare roll 2, the entire bank of kneading mass 3 and part of the roll 1 covered with the rolling sheet can be scanned. The infrared radiation receiver 5 is coupled with a recorder 7. In the recorded radiation corve the two points of transition of rolling sheet to kneading mass 8 and of kneading mass to bare roll 9 are marked as points of discontinuity, the distance of which indicates the thickness of kneading mass.

FIG. 2 shows a recorded radiation curve in which $a$ denotes the thickness of kneading mass, $b$ indicates the surface temperature of the kneading mass and $c$ indicates the surface temperature of the rolling sheet.

What is claimed is:

1. A process for measuring without contact the thickness of a thermoplastic mass having a temperature of at least 40°C in the manufacture of a sheeting on a calender having an accumulation of material kneading mass, in the feeding region of a roller gap having a pair of pressure elements at least one of which is a roller, one of the pressure elements forming the gap being covered by the sheeting in the region of the gap and other pressure elements being bare of sheeting and kneading mass in the feeding region of the gap, the process comprising the steps of scanning at a predetermined scanning speed the region in discrete areas having a diameter of from 0.5 to 3 mm over a scanning range of from 0.2 to 3 m in a zone extending over the transitions from bare pressure element surface to kneading mass to sheeting with an infrared radiation sensor having a small field of view capable of scanning the discrete area diameters from 0.5 to 3 mm, plotting the curve of thermal radiation detected by the sensor at a predetermined plotting speed, measuring in the plotted curve the distance "$a$" of two points of discontinuity which occurs at the transitions between kneading mass and sheeting and kneading mass and bare pressure element, and multiplying the measured distance with the quotient of the scanning speed and the plotting speed to obtain the absolute thickness of the accumulated material kneading mass.

* * * * *